Figure 1:
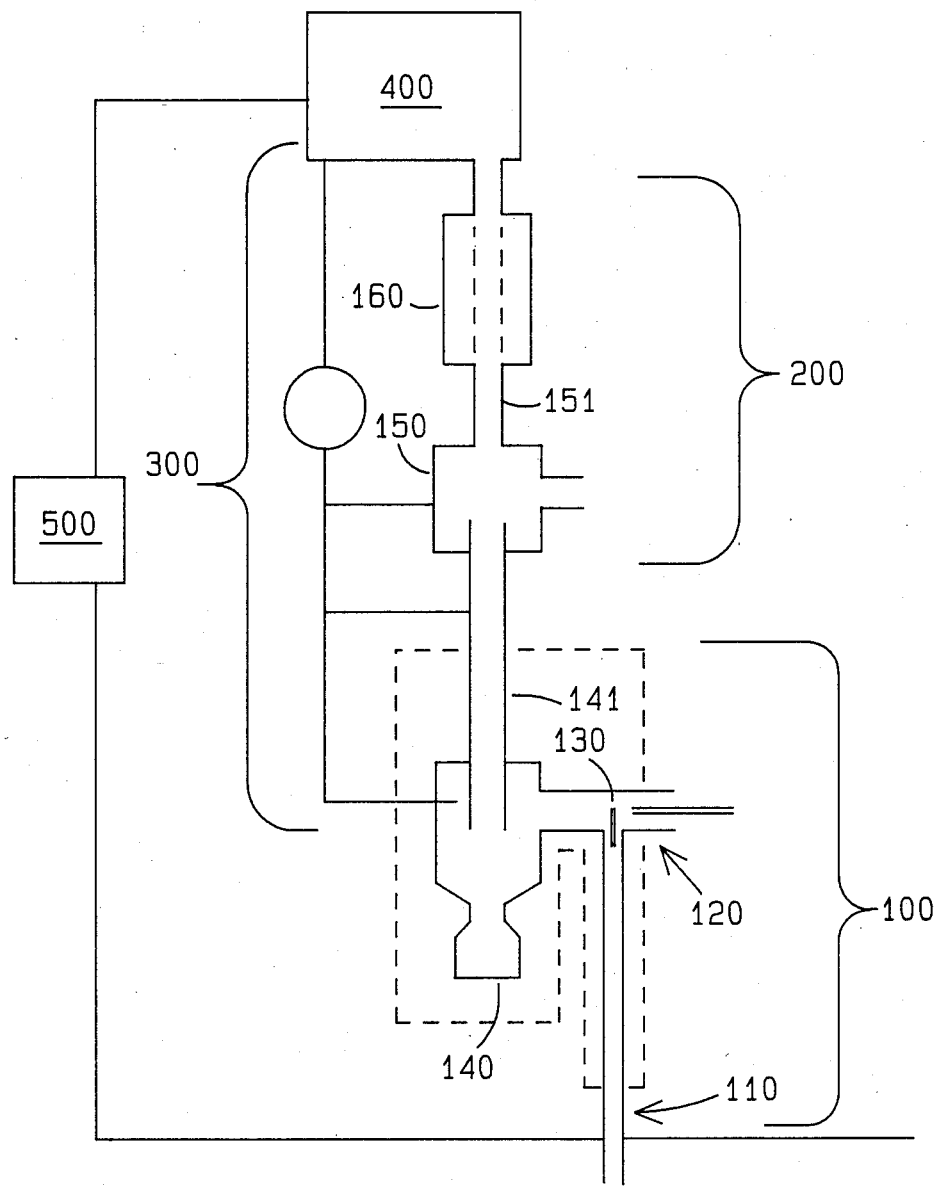

United States Patent [19]

Alvarez et al.

[11] Patent Number: 4,806,150

[45] Date of Patent: Feb. 21, 1989

[54] DEVICE AND TECHNIQUE FOR IN-PROCESS SAMPLING AND ANALYSIS OF MOLTEN METALS AND OTHER LIQUIDS PRESENTING HARSH SAMPLING CONDITIONS

[75] Inventors: Joseph L. Alvarez, Idaho Falls; Lloyd D. Watson, Rigby, both of Id.

[73] Assignee: The United States Department of Energy, Washington, D.C.

[21] Appl. No.: 146,641

[22] Filed: Jan. 21, 1988

[51] Int. Cl.$^4$ ................................................. B22F 9/08
[52] U.S. Cl. ..................................... 75/0.5 C; 264/12; 425/6; 425/7
[58] Field of Search ............................ 75/0.5 B, 0.5 C; 264/12; 425/6, 7

[56] References Cited

U.S. PATENT DOCUMENTS

| 2,793,282 | 5/1957 | Steigerwald | 425/6 |
| 3,077,307 | 2/1963 | Moore et al. | 425/6 |
| 3,430,289 | 3/1969 | Aikawa et al. | 425/6 |
| 3,602,595 | 8/1971 | Dahlquist et al. | 356/36 |
| 3,659,944 | 5/1972 | Bojic | 356/86 |
| 3,669,546 | 6/1972 | Virlogel | 356/86 |
| 3,672,774 | 6/1972 | Bojic et al. | 356/86 |
| 4,578,022 | 3/1986 | Kenney | 425/6 |

*Primary Examiner*—Wayland Stallard
*Attorney, Agent, or Firm*—Hugh W. Glenn; Robert J. Fisher; Judson R. Hightower

[57] ABSTRACT

An apparatus and method for continuously analyzing liquids by creating a supersonic spray which is shaped and sized prior to delivery of the spray to a analysis apparatus. The gas and liquid are mixed in a converging-diverging nozzle where the liquid is sheared into small particles which are of a size and uniformly to form a spray which can be controlled through adjustment of pressures and gas velocity. The spray is shaped by a concentric supplemental flow of gas.

15 Claims, 4 Drawing Sheets

DEVICE AND TECHNIQUE FOR IN-PROCESS SAMPLING AND ANALYSIS OF MOLTEN METALS AND OTHER LIQUIDS PRESENTING HARSH SAMPLING CONDITIONS

CONTRACTUAL ORIGIN OF THE INVENTION

The U.S. Government has right in their invention pursuant to Contract No. DE-AC07-76IDO1570 between the U.S. Department of Energy and EG&G Idaho, Inc.

TECHNICAL FIELD

The present invention relates to a means for testing liquids and more particularly a method and apparatus for sampling molten metals and the like on a continuous basis.

BACKGROUND OF THE INVENTION

Many industries require complicated manufacturing processes that must be conducted in a remote, automatic manner made necessary by the harsh conditions of the process. The end result of the process may generally be known only with some degree of uncertainty and is usually determined by stopping the process and analyzing a sample. A decision is made, based on the sample, to continue, discontinue, or alter the process. Costs and productivity can be affected by the timeliness of and time required for the sampling and testing, as well as the accuracy of the analysis. The metals industry is indicative of such concerns, as evidenced by an increasing need for on-line analysis of molten metal. Such analytical needs generally require that a restricted access to be maintained to the process even with the harsh conditions, and generally involves a long sampling and analysis time compared to the time of the process. The need for on-line analysis has increased in the metals industry due to an increasing use of continuous processing. In addition, the need for higher quality metal alloys has increased, total process lines have shortened, and energy costs have increased.

The present practice of the metal industry is to extract a sample from the melt at the predicted end of the refining process. The sample is rapidly cooled and transported to a laboratory for analysis. The process metal remains at temperature and continues its chemical activity during the analysis time. After the testing of the sample is complete, the metal is poured if the correct elemental ratios exist; further refining takes place if the testing indicates.

The ferrous metals industry represents some of the harshest sampling conditions and the largest volume of the metal industry. Several attempts have been made to provide rapid, in-process, elemental analysis of molten steel. Such analyses were based on taking emission spectra from the metal surface after excitation by ultraviolet or plasma methods and are described in U.S.Pat. Nos. 3,645,638; 3,659,944; 3,669,546; and 3,672,774. The lack of success in applying these techniques may be attributed to problems with optical coupling and the maintenance of delicate spectroscopic systems, cleaning and positioning of the excitation volume, and differential vaporization in the excitation volume.

Efforts to avoid the above problems were made by extracting the liquid metal in particulate form, as set forth in U.S. Pat. Nos. 3,606,540; 3,602,595; and 4,578,022.

A critical problem with past efforts using atomized metal powders in continuous elemental analysis procedures of liquid metals has been metal buildup on the inside of the probe wall. Such metal buildup can completely clog the probe core in a matter of minutes. Once clogged, these earlier probes had to be discarded after as few as one analysis procedure. To compensate for metal buildup on the internal probe walls of previous designs, extraordinary supplementary gas flow procedures as set forth in U.S. Pat. No. 3,606,540 were taken by others with minimal success.

DISCLOSURE OF INVENTION

Figure 4:
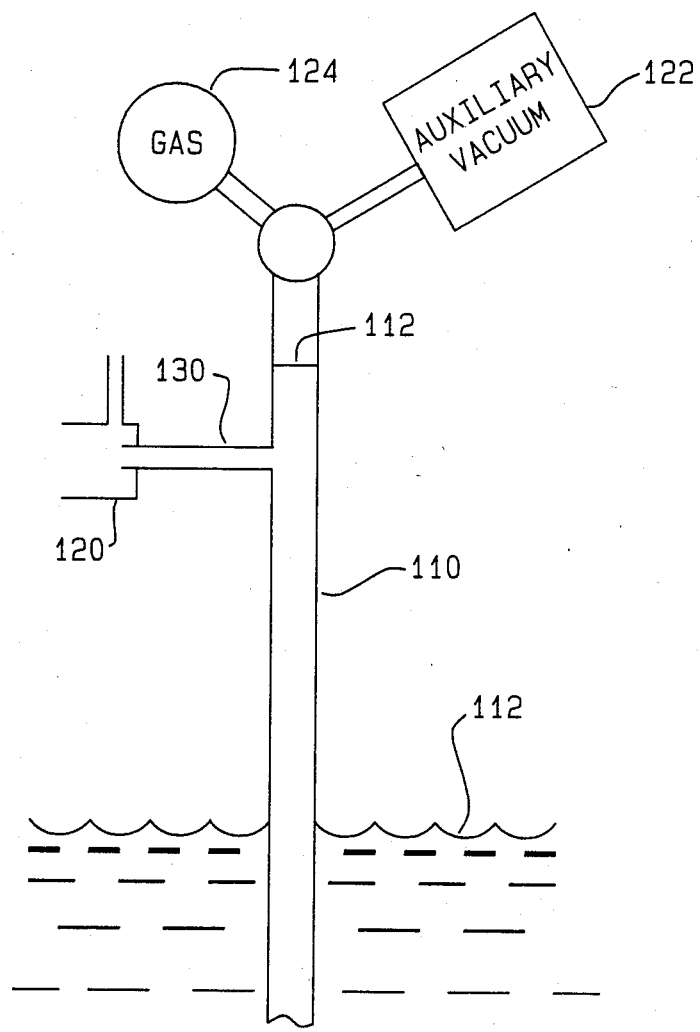

The present invention provides a probe apparatus for extracting a liquid sample, nebulizing and rapidly cooling the sample in a cooled nebulizing chamber, and rapidly transporting the nebulized sample through a transport and sample conditioning system to an analysis system. In a preferred embodiment, the invention includes a heated, refractory extraction tube, a heated, refractory nebulizing tube drawing the sample to the nebulizing nozzle and a sheathed gas delivery system for shaping and rapidly cooling the nebulized spray. The spray is directed into a cooled chamber for particle sizing. The spray is directed from the cooled chamber by a sample transport system to a sample conditioning and control system for gas clean up, particle concentrating and sizing, and flow and pressure control. In this manner, an adequate, uncontaminated, representative sample is delivered to the analytical apparatus, without clogging the probe walls.

BRIEF DESCRIPTION OF THE DRAWINGS

These and other objects and features of the invention will be more readily understood by consideration of the following detailed description taken with the accompanying drawings, in which:

FIG. 1 is a schematic overview of the liquid extraction and nebulizing probe and condition and transport system used to produce the aerosol sample for introduction into the analyzing system.

FIG. 2 is a cross-section of one embodiment of the subject invention showing a nebulizing and spray shaping and cooling apparatus.

FIG. 3 is a cross-section of another embodiment of the subject invention showing a nebulizing and spray shaping and cooling apparatus.

FIG. 4 is a detailed view of another embodiment of the subject invention which shows a liquid extraction system with heating elements to maintain bulk conditions to prevent solidification or precipitation.

FIG. 5 is a schematic of a nozzle which may be used with the subject invention.

DESCRIPTION OF SPECIFIC EMBODIMENTS

Specific embodiments of the invention are described below with respect to molten metals; however certain specific alterations in the procedure may be required for different liquids. In other words, in certain applications an opposite effect may be required in a given step to prevent sample alteration, e.g., cooling instead of heating.

FIG. 1 is a perspective view of the sampling and analysis system of the subject invention, including a means for extracting, nebulizing, and cooling 100, a particle sizing probe 110; a sample transport and conditioning system 200, a sample flow control system 300, a sample analysis system 400, and a process feed back control system 500 are shown. The probe 110 comprises a refractory, heated extraction tube for delivery of the liquid to a nebulizing nozzle 120. The liquid may be extracted from the liquid pool by vacuum from the nebulizing nozzle or from an auxiliary vacuum pump as shown in FIG. 4. The nebulizing nozzle 120 has a liquid feed tube 130 constructed from the same material as the nozzle 120. In the alternative, the feed tube may be a refractory metal or ceramic insert for transporting the liquid from the extraction tube 110 to the nozzle 120. The feed tube 130 may require heating to prevent solidification or precipitation on the tube walls due to cooling by the nebulizing gas.

The fluid pressure presented to the nebulizing nozzle is static and may be maintained in the various embodiments by positioning the probe height relative to the surface level 112 of the liquid such that the nozzle to surface distance is held constant. In the event that the liquid surface level 112 is highly variable or that the sample must be raised higher than the aspirating ability of the nozzle, an auxiliary vacuum system 122 may be connected to the extraction tube, as shown in FIG. 4.

A controlled head is also possible by holding the liquid at a set level above the liquid level 112. The extraction tube 110 has a small diameter to reduce surface effects on the liquid and minimize the volume of the sample taken. The extraction tube 110 is made of a refractory material and is preferably nonwetting. The extraction tube should be purged by inert gas after each sampling cycle either by back pressurizing the nebulizing nozzle or from a gas line 124 connected to the vacuum control system as shown in FIG. 4.

Figure 2:
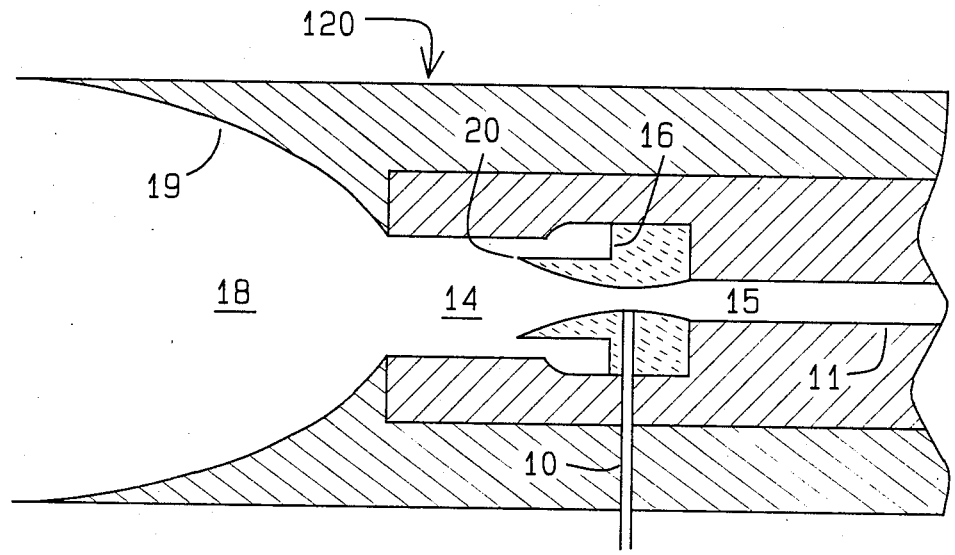
Figure 3:
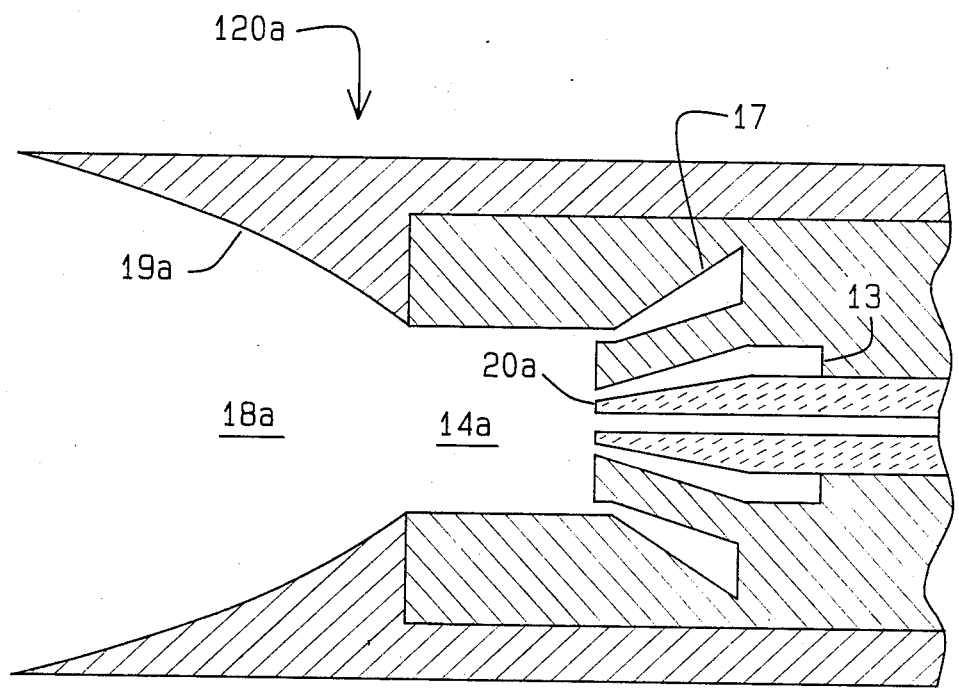

As shown in FIGS. 2 and 3, the nebulization of the sample is accomplished with a nozzle 120, 120a having a gas nebulizing die 20, 20a. The gas used should be inert to the liquid system and would normally be argon or nitrogen, although it could be air, steam, or any other, as long as it does not interfere with the analysis of the sample or corrode or erode the sampling system. In another application, the gas may be chosen to react with the sample, should this prove to stabilize the sample or convert it to a more easily transportable or analyzable form. The gas may be heated or otherwise temperature controlled to minimize temperature effects on the spray or liquid feed. Heating of the gas should pevent freeze off of the liquid metal feed.

The gas nebulization nozzle include embodiments 120 and 120a as will be described in connection with FIGS. 2 and 3. The choice of the particular embodiment to be used is dependent on construction materials, temperature of the liquid, efficiency of droplet production, and mounting conditions. The material choice and shaping of surfaces and passages is also temperature and temperature gradient dependent. Choices will be made on the basis of minimizing thermal shock and stress. Both embodiments may require a high velocity sheathing gas for shaping of the flow and cooling of the droplets.

In the first embodiment shown in FIG. 2, the nebulizing gas is directed orthogonally to the liquid feed 10 through gas feed or plenum 11 in such a manner that the resulting droplet laden stream is directed toward the entrance of the particle sizing system. In the second embodiment shown in FIG. 3, the nebulizing gas is delivered generally in parallel and surrounding the liquid feed 12 through gas feed 13 and directed toward the axis of the liquid feed such that the gas stream intersects the liquid feed axis after the terminus of the liquid feed.

In both embodiments the gas plenums 11 and 12 are pressurized, causing the liquid to be drawn into the nebulizing chambers 14 and 14a solely by the aspirating effect of the nebulizing gas. The amount of pressure may be made variable, so that the gas to liquid ratio is variable and therefore the amount of liquid nebulized is variable. This latter effect allows a selection in the particle size distribution produced or total size of the sample produced or both.

The liquid feed may be lined with a removable refractory material (not shown) so that it may be replaced to allow for compatibility with the liquid being sampled and for extension of the life of the nebulizing die. The plenum or gas annulus 13 of FIG. 3 has a size and shape which will minimize resistance to flow as known in the art. Plenum 13 tapers to the initial diameter or thickness of the annular nozzle. The sides of the plenum 13 slope, each at a different angle. The plenum terminates at the face of the liquid feed. This structure permits a smooth liquid flow to the nozzle and equal distribution of the nebulizing gas in the plenum and about the annulus.

The shape of the gas nozzle and the placement of the liquid feed is important to the operating characteristics of the die and affects the particle size distribution and the shape of the spray. Both nozzles may be shaped with converging and diverging sections so as to provide a super sonic two phase flow.

In the apparatus and method of the subject invention, the liquid and gas are fed into the nozzle such that the two phases (gas and liquid) mix at or around the gas choke point and enter the diverging section of the nozzle where the two phase mixture expands and utilizes some of the energy of expansion to push the two phase mixture into supersonic speed.

Figure 5:
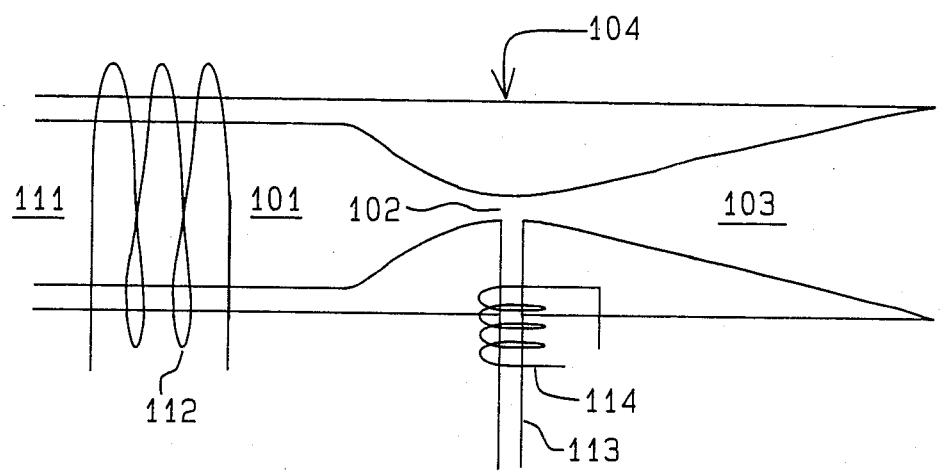

FIG. 5 shows a schematic of a nebulizing nozzle for use in the subject invention as depicted in FIG. 2. This nozzle has a gas inlet portion 101 of a nozzle which converges to a minimum at the choke point 102 and then diverges outwardly in the exit portion 103 of the nozzle. Suitable gases which may be used in the subject invention are those gases which are compatible with the material to be sprayed, as well as with the materials of the spraying apparatus. Such gases are generally the inert gases, such as Argon, Nitrogen, Helium, Neon, and the like. Other gases, such as air, may be functional in limited applications.

In FIG. 5, the nebulizing gas is introduced to the units through the gas feed 111. The gas feed 111 may be temperature controlled by elements 112. The gas feed terminates at the converging portion where the choke point 102 of the converging-diverging nozzle 104. The liquid feed 113 may also be temperature controlled by heating elements 114. While shown as being located orthogonally near or about the narrow or choke point 102 of the nozzle 104, the liquid may also be parallel to the gas feed. The exact location of liquid feed 113 may vary dependent primarily on the proportion or species of the components involved and may also depend on the sonic velocity of the two-phase mixture and the amount of aspiration at the liquid outlet desired, and thus the location of the liquid feed 113 may be adjusted relative to the choke point. Such relative placement will affect spray shape and dimensions, liquid throw, spray placement, and other spray parameters. Though the liquid feed 3 in FIG. 5 is shown to enter from one side, it may enter from either side or both sides simultaneously. The shape and size of the diverging section of the nozzle 103 can have a length, shape and degree of divergence dependent upon the sonic velocities of the two-phase mixture, the desired characteristics of the exiting stream and droplet size distribution.

As stated, the position of the end of the liquid feed 113 of FIG. 1 will affect the spray characteristics. The liquid feed 3 can be positioned to the rear or the front within the choke point 102, thereby increasing or decreasing the amount of aspiration or back pressure of the liquid feed, which will determine the flow rate of the liquid when considered in combination with the liquid pressure. The amount of flow can thus be controlled by varying liquid pressure, nozzle exit pressure, gas flow, and pressure. This will allow control of the spray pattern, plume density and droplet size distribution during the process as conditions or requirements vary, and can be utilized in conjunction with adjustment of the position of the liquid inlet relative to the choke point to further control the spray.

Another manner of controlling the spray is to control the temperature of either or both the liquid and gas feeds. This control may be necessary to prevent freezing of the liquid in the liquid feed or freezing within the nozzle before all necessary conditions are established. A further consideration in temperature control is that sonic conditions are temperature dependent and dependent upon the degree of thermal equilibrium between the phases. A further need for the temperature control is to vary the droplet temperature at the exit, to compensate for heating or cooling from phase interactions, and to compensate for cooling from expansion.

The flow shaping in the first embodiment of the subject invention (FIG. 2) causes a focusing of the two phase flow into a narrow region centered about the longitudinal axis of the nozzle. Such focusing is primarily the result of the terminus of the liquid feed 10 being located at or about the narrow throat 15 of the nozzle, with the liquid flow direction being orthogonal to the gas flow direction.

The flow shaping in the second embodiment (FIG. 3) causes liquid to flow along the face of the die 20a to the gas annulus because of entrained gas flow at the point of detachment. The droplet laden jet that results after the intersection of the annular jet is directed along the axis of the liquid feed die 20a by the gas flow, but is not as well confined as the first embodiment.

A secondary gas flow is introduced annularly in passages 16 (FIG. 2) and 17 (FIG. 3) concentric with the gas feeds 11 and 13 respectively. This secondary gas flow further constrains the spray to a narrow region along the nozzle axis. The secondary gas is introduced as a sheathing gas along the tube which conducts the droplets to the article sizing system. The sheathing gas may be introduced at a minimal quantity as a laminar layer, or as a high speed, expanding jet that is just sufficient to confine within its parameters the largest expected droplet moving at the highest expected velocity. This secondary gas flow will provide additional cooling to the primary spray and reduce the amount of vaporization of volatiles in the spray because of this added cooling. The flow tubes 18 and 18*a* expand smoothly, but abruptly, after the spray has been sufficiently confined to prevent deposition on the tube walls 19 and 19*a*. Such expansion cools the gas and the liquid to the point of solidification if molten metals are involved. The sheathing gas may be eliminated for some materials, if the flow is sufficiently focused down the flow tube and additional cooling is not necessary. Sufficient heating or cooling may be accomplished by heat exchange to the flow tube walls.

The construction of the extraction tube 110, nebulizing die 20, 20*a*, and shaping chamber 18, 18*a* is such that the amount of high temperature material is minimized, as is the number of high temperature sealing surfaces. The nebulizing die and shaping chamber is mounted to the transport tube via an air or water cooled metal mount with an intervening sealing material (not shown) capable of withstanding sharp temperature gradients, such as silicone rubber or the like. This sealing material seals all joints and adjacent surfaces in contact with either liquid or gas.

Referring again to FIG. 1, the particle laden stream passes through a transport tube 131 after the flow shaping chamber. The length of the transport must be sufficient to cool the particles to solidification or to a certain temperature that will affect particle sizing in a desired manner. Particle sizing may be accomplished in appropriate devices for the size and conditions necessary for further transport and analysis of the particle, such as a cyclone 140 or a virtual impactor 150. Either cyclone or virtual impactor can be constructed in a manner known in the art to return the rejected particles to the bulk liquid either continuously or after a set collection period. The transport line and particle sizing device may be protected from the bulk liquid as necessary by refractory material, insulation, cooling or the like (not shown). The transport line and particle sizing device are normally suspended above the bulk liquid, but could be immersed partially or totally in the liquid, as necessary.

The transport system comprising lines 141 and 151 is located directly after the particle sizing device, and is principally narrow bore tubing of only the minimum length necessary to reach the analysis system 400. The transport system is arrayed in a manner known in the art to maximize particle transport, and includes sample conditioning equipment 160 to prepare the sample for introduction into the analysis system 400. In one embodiment, a sample concentration system includes a virtual impactor that concentrates particles inertially in a minimum gas flow while allowing vapors and smaller, nonrepresentative particles to continue with the majority flow; thus, the sample concentrating system may allow further selection of the representative and transportable particle size. Another embodiment for sample conditioning is a gas and vapor clean up system that would remove interfering gases and vapors or dry the particles for improved analysis of the sample. This system includes one or more absorptive and/or reactive materials such as activated charcoal, calcium chloride, or the like, placed annularly around a porous section of the transport tube. The contaminating gases and vapors are removed by diffusion to the absorptive or reactive media.

The analysis system 400 is located in line with the transport system. The analytical apparatus may be any commercially available device which includes the necessary flow control to be compatible with the required measurements. The apparatus should require no further alteration of the sample and should allow direct injection as do plasma emission devices or atomic absorption devices. Apparatus requiring chemical reaction for chemical rather than elemental information may be used, as may similar reaction systems for eliminating or separating interfering species.

A control system (not shown) may be imposed on part of or the total system. This control system may use reference signals for control, the output of the analysis system, and/or flow, pressure, or temperature of any part of the sampling and transport system or any combination of these signals. The control system may obtain its results by direct feed back or forward feed of the signals or the information may be processed by computed means. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

What is claimed:

1. A method for delivering a liquid to a means for continuously analyzing the liquid comprising the steps of:

directing the liquid into a stream of a gas, nebulizing the liquid into discrete particles, forming a two phase spray of the gas and liquid particles, shaping and cooling the spray by directing a supplemental gas flow concentrically about the spray;

directing the shaped and cooled spray to a particle sizing means;

directing the sized particles to a conditioning means; and analyzing the sized and conditioned particles.

2. The method of claim 1 wherein said liquid is orthogonally directed into said stream of gas.

3. The method of claim 1 further including the step of converging said gas stream to contact said liquid and form said two phase spray and diverging said spray at supersonic speeds.

4. The method of claim 1 wherein said step of directing said spray to a particle-sizing means includes controlling the temperature of said spray.

5. The method of claim 1 further including the step of heating the stream of gas.

6. The method of claim 1 further including the step of pressurizing the stream of gas.

7. The method of claim 6 further including controlling the pressure of the stream of gas to control the particle size of the spray and the volume of liquid sprayed.

8. In an apparatus for testing liquids, a means for continuously sampling a liquid, said sampling means comprising a liquid feeding means and a gas feeding means;

said liquid feeding means delivering liquid into a nebulizing means of a nozzle apparatus and said gas feeding means delivering a gas under pressure through a converging area of gas flow into said nebulizing means of said nozzle apparatus;

said liquid mixing with said gas within said nebulizing means to form a two phase spray, a diverging area in said nozzle apparatus for the travel of said spray upon forming, whereby said spray is induced to travel at supersonic speeds;

a means for shaping said spray to restrict and shape the spray, thereby reducing the dispersal of the spray and preventing the deposition of the spray on said nozzle apparatus; and a transport tube for delivering the spray to a particle conditioning means for sizing and preparation of said spray prior to analysis of said spray.

9. The apparatus of claim 8 wherein said liquid feeding means comprises an extraction tube oriented orthogonally to said gas feeding means.

10. The apparatus of claim 8 wherein said gas feeding means is concentric with said liquid feeding means.

11. The apparatus of claim 8 wherein said liquid is a molten metal.

12. The apparatus of claim 8 wherein said gas is an inert gas selected from the group consisting of argon and nitrogen.

13. The apparatus of claim 8 wherein said nozzle apparatus has a converging portion prior to the entry of said gas and a diverging portion for the travel of the spray.

14. The apparatus of claim 8 wherein said gas is temperature controlled.

15. The apparatus of claim 8 wherein said means for delivering liquid is lined with a refractory material.

* * * * *